US006979689B2

(12) United States Patent
Gonzales et al.

(10) Patent No.: US 6,979,689 B2
(45) Date of Patent: Dec. 27, 2005

(54) COMPOSITIONS AND METHODS FOR TREATING UPPER RESPIRATORY CONGESTION

(75) Inventors: Gilbert R. Gonzales, New York, NY (US); Thomas P. Jennings, Cleves, OH (US); Norman D. Schellenger, Midloathian, VA (US)

(73) Assignee: PediaMed Pharmaceuticals, Inc., Florence, KY (US)

( * ) Notice: Subject to any disclaimer, the term of this patent is extended or adjusted under 35 U.S.C. 154(b) by 0 days.

(21) Appl. No.: 10/324,425

(22) Filed: Dec. 20, 2002

(65) Prior Publication Data

US 2004/0122022 A1    Jun. 24, 2004

(51) Int. Cl.$^7$ ............... A61K 31/44; A61K 31/135; A61K 31/13
(52) U.S. Cl. ................ 514/282; 514/653; 514/648
(58) Field of Search ............... 514/282, 653, 514/648

(56) References Cited

U.S. PATENT DOCUMENTS

| 5,458,879 | A | * | 10/1995 | Singh et al. ............... 424/400 |
| 5,681,577 | A |   | 10/1997 | Lech et al. |
| 6,160,020 | A | * | 12/2000 | Ohannesian et al. ........ 514/629 |
| 2003/0049318 | A1 | * | 3/2003 | Davis et al. ............... 424/468 |
| 2003/0077321 | A1 | * | 4/2003 | Kiel et al. ................. 424/465 |
| 2004/0029864 | A1 | * | 2/2004 | MacMillan ............ 514/217.05 |
| 2005/0020509 | A1 | * | 1/2005 | Kiel et al. ................ 514/23 |

FOREIGN PATENT DOCUMENTS

| WO | WO 85/04589 | 10/1985 | .......... A61K 45/06 |
| WO | WO 94/8870  | 12/1994 | .......... A61K 9/00  |
| WO | WO 95/07103 | 3/1995  | .......... A61K 45/06 |

OTHER PUBLICATIONS

Complete Drug Reference, 1995, pp. 306-309.*
MEDLINE 1998358208, McLeod et al, Pharmacology, Aug. 1998 57 (2) 57-64, abstract.*
MEDLINE AN 83227600, Lang et al, Advances in Neurology 1983 37 193-200, abstract.*
MEDLINE AN 96216810, Di Pietra et al, J. Chromatography Apr. 5, 1996 729(1-2) 355-61, abstract.*
EMBASE AN 78384809, Massoud, J. Pediatrics 1978 Feb. 1993 308, abstract.*
CA59:28335, BE 622696 19630115, abstract.*
WPIDS AN 1985-146685, Sunshine et al, BE901667 19850529, abstract.*
DRUGU AN 2001-22049, Raffa R, J. Clin. Pharm. Ther., 26(2) 81-85, 2001.*
DRUGU AN 1989-19247, Wolters et al, Can. Med. Asooc. J., 140(5) 507-13, 1989, abstract.*
MEDLINE AN 97217824, Humphries et al, J burn care & rehab., Jan.-Feb. 1997, 18 (1 pt 1) 34-6, abstract.*
*Endal®HD Syrup*, <URL http://www.axisvisual.com/ed/pages/syrup.html> pp 1-2 Oct. 21, 2002.
*Endal® HD Plus Syrup*, <URL http://www.axisvisual.com/ed.pages/syrup_plus.html> pp 1-3 Oct. 21, 2002.
*Endal® Time Release Tablets Nasal Decongestant*, <URL http://www.axisvisual.com/ed/page/nasal.html> pp 1-2 Oct. 21, 2002.
*Endal® Expectorant*, <URL http://www.axisvisual.com/ed/pages/expectorant.html> pp 1-2 Oct. 21, 2002.
International Search Report, mailed Jun. 2, 2004.
Storms et al. *,SCH 434: A new antihistamine/decongestant for seasonal allergic rhinitis*, Journal of Allergy and Clinical Immunology, Mosby , vol. 83, No. 6, Jun. 1989, pp. 1083-1090, XP000990053.
Barris, *Use of Benadryl for Symptomatic Relief of "Thalamic Pain"*, Neurology, 2 (1952), 59-64.
Bluhm, et al., *Potentiation of Oploid Analgesia by $H_1$ and $H_2$ Antagonists*, Life Sciences, 31 (1982), 1229-1232.
Santiago-Palma et al., *Diphenhydramine as an Analgesic Adjuvant in Refractory Cancer Pain*, Journal of Pain and Symptom Management, 22:2 (2001), 699-703.
Rumore et al., *Clinical Efficacy of Antihistamines as Analgesics*, Pain, 25 (1986), 7-22.
Rumore, et al., *Analgesic Effects of Antihistaminics*, Life Sciences, 36:5 (1985), 403-416.

* cited by examiner

*Primary Examiner*—Rebecca Cook
(74) *Attorney, Agent, or Firm*—Wood, Herron & Evans, L.L.P.

(57) ABSTRACT

A composition of an antitussive, a decongestant, and diphenhydramine as an antihistamine to treat upper respiratory and oral pharyngeal congestion and related symptoms in a patient. In addition to providing antihistamine effects, diphenhydramine also provides effects as an anti-cholinergic, an analgesic, an antitussive, and an analgesic adjuvant.

53 Claims, No Drawings

COMPOSITIONS AND METHODS FOR TREATING UPPER RESPIRATORY CONGESTION

FIELD OF THE INVENTION

The present invention relates to the treatment and relief of various symptoms of upper respiratory and oral pharyngeal congestion, and in particular, to a combination medication for treatment and relief thereof.

BACKGROUND OF THE INVENTION

People around the world frequently suffer from upper respiratory tract and oral pharyngeal congestion. This congestion may be caused by allergies, infections in the respiratory tract and/or oral and pharyngeal cavities, changes in weather conditions, as well as from the overall health and genetic disposition of the person. This congestion is generally diagnosed from partially or fully blocked air passages including airways in the lungs, mouth, nose, and throat. Other symptoms related to the cause typically accompany the congestion. Cough, tickles in the throat, cold symptoms such as fever, flu, sinus infections, and throat or gland pain are some of the more common symptoms found with upper respiratory and oral pharyngeal congestion.

Congestion of the upper respiratory tract and oral pharyngeal cavity and related symptoms generally have undesirable effects for the afflicted person. For example, the congestion may affect performance in the workplace, school, and at home up to and including loss of work and loss of school attendance. Further, congestion may reduce the ability to perform routine activities, such as housework, driving, running errands, and may even totally incapacitate the person. Severe and intolerable congestion often requires visits to the hospital and treatment. In addition, viral or bacterial infections of the sinus passage or other airway may be passed to healthy persons through symptoms of the congestion. For example, a cough or sneeze may convey a bacterium or virus to another person. Thus, upper respiratory tract and oral pharyngeal congestion and its symptoms need to be treated.

Generally, there are two typical approaches to treating symptoms of the congestion. One approach involves initially treating the underlying cause of the symptom. For example, a bacterial infection is generally treated by administering an antibiotic to kill the bacteria causing the infection. The second approach involves treating the symptoms themselves, typically in addition to treating the underlying cause, by independently administering one or more medications for relief of specific symptoms. For example, an antitussive agent, commonly referred to as a cough suppressant, has been typically administered for the treatment or relief of cough. An opioid medication, such as codeine and hydrocodone bitartrate, has generally been administered to relieve pain consistent with the congestion while suppressing a cough. Also decongestants, such as phenylephrine and pseudoephedrine, have been administered to both children and adults in flavored formulations for reducing mucosal swelling and draining the mucus build-up to clear congestion in the air passages. Symptoms due to allergies or allergens are often treated with an antihistamine. Antihistamines, often referred to as histamine-class receptor blockers, are compounds that may antagonistically block the histamine receptor from binding histamine thereby preventing the symptoms of an allergy. Examples of antihistamines include bromphen-eramine maleate, chlorpheneramine maleate, and diphenhydramine, all of which have shown good clinical efficacy.

There are many different treatment medications utilizing a combination of agents in therapeutic doses for treating multiple symptoms of upper respiratory tract and oral pharyngeal congestion. As one example, a single medication may include an expectorant, in combination with an antitussive agent, for removing phlegm or mucus that may have accumulated in the lungs and other air passages in addition to suppressing a cough. The expectorant is helpful in preventing the progression of a mild case of bronchitis to a more severe case of pneumonia. As another example, an opioid medication such as hydrocodone bitartrate may be combined with a decongestant, such as phenylephrine, to provide relief from congestion and discomforts related to the congestion. In addition, antihistamines may be included with the opioid and the decongestant in a single medication. For example, chlorpheniramine may be included as an antihistamine with hydrocodone and phenylephrine in a single medication.

Combination therapy provides many benefits. For example, it allows patients suffering from congestion and related symptoms to take only a single dosage medication, as opposed to multiple medications, for relief therefrom. Further, it enhances compliance in accordance with a regimen by eliminating the need for the patient to take different medications. To this end, combination therapy provides convenience, ensures compliance, and saves cost.

Combined treatment medications may be formulated as syrups, pills, tablets, and capsules. Formulations may include flavoring agents to mask undesirable flavors or tastes from desired medicinal agents and colorants to render the medication more attractive and appealing to the eye. For example, many formulations have a raspberry, cherry, orange, or grape flavor well liked by both children and adults. Moreover, these flavors are easily identified by their color. In combination formulations, the individual ingredients are included in amounts proven to be effective to treat targeted symptoms. Effective amounts have varied depending on the particular formulation, type and degree of the symptoms, and desired user or consumer. For example, a child's dose of an elixir or syrup for the relief of cough and pain related to congestion may have the antitussive and analgesic in reduced quantities based on size, weight, and age of the child targeted, comparable to a composition or formulation for an adult which may have double the dosage of the antitussive and analgesic.

Accordingly, it is desirable to have an administrable composition to reduce symptoms of upper respiratory tract and oral pharyngeal congestion. It is further desirable that the composition be effective in reducing cough, congestion, histamine-stimulated allergy symptoms and related pain. Still further, it is desirable for the composition to contain dosages suitable for administration to a child as well as an adult. In addition, it is desirable to have the composition in a convenient and pharmaceutically acceptable dosage form.

SUMMARY OF THE INVENTION

The present invention provides compositions and methods for treating upper respiratory and oral pharyngeal congestion and related symptoms in a person suffering therefrom. To this end, and in accordance with the principles of the present invention, there is provided a composition of an antitussive, a decongestant, and diphenhydramine or pharmaceutically acceptable salt thereof as an antihistamine. The combination of an antitussive, a decongestant, and diphenhydramine in a single composition provides relief of cough, congestion in the air passageways, and common allergy-type symptoms resulting from exposure to various allergens, in a convenient and effective dosage formulation.

The inclusion of the diphenhydramine provides not only relief of allergy symptoms as an antihistamine, but also acts as an anticholinergic agent and as an analgesic adjuvant to enhance the effect of an analgesic that is either additionally present in the composition or is independently administered. In addition, diphenhydramine has properties that have been characterized as mildly sedative, mildly antitussive, and mildly analgesic. Amounts of the diphenhydramine in the inventive composition are within a dosage range from about 3 mg to about 100 mg in a single dose of the formulation. In one embodiment, diphenhydramine in the composition is within a range from about 3 mg to about 25 mg for a child, and from about 12 mg to about 100 mg for an adult.

The antitussive may be a known antitussive agent, such as hydrocodone or a pharmaceutically acceptable salt form, for inclusion in the composition. In one embodiment, the antitussive is present in the formulation in an amount in the range from about 0.5 mg to about 15 mg in a single dose of the formulation. In another embodiment, the antitussive is present a single dose of the formulation in an amount ranging from about 0.5 mg to about 8 mg for a child, and from about 2 mg to about 15 mg for an adult. Similarly, the decongestant may be any conventionally known and pharmaceutically accepted decongestant, such as phenylephrine for example. In one embodiment, the decongestant is present in the formulation in an amount ranging from about 1 mg to about 20 mg in a single dose of the formulation. In another embodiment, the decongestant is present a single dose of the formulation in an amount ranging from about 1 mg to about 10 mg for a child, and from about 5 mg to about 20 mg for an adult. The amounts or the antitussive, decongestant, and diphenhydramine desired may vary, advantageously within the ranges provided, depending upon formulation, intended use, patient age, patient weight, etc.

The composition is formulated in pharmaceutically acceptable forms such as liquids, pills, capsules, tablets, and the like. Suitable capsule forms include, without limitation, liquid gelatin capsules and enteric-coated capsules. The tablet form may be chewable, may melt or disintegrate in the mouth, or may be enteric-coated to provide delayed-release and sustained-release characteristics for the composition. In one embodiment, the composition is formulated into a liquid. The composition may further include other components, such as conventional excipients including binders, colorants, fragrances, and the like, to render the composition more attractive and suitable for use.

By virtue of the foregoing, there is thus provided compositions and methods for treating upper respiratory and oral pharyngeal congestion and related symptoms in effective formulations. These and other benefits and advantages of the present invention shall be made apparent from the accompanying detailed description thereof.

DETAILED DESCRIPTION OF THE INVENTION

The present invention provides compositions and methods for treating upper respiratory and oral pharyngeal congestion and related symptoms in a patient in need thereof. The term "upper respiratory and oral pharyngeal congestion" as used herein includes congestion in the oral, pharyngeal, nasal, and bronchial passages of the upper respiratory tract. It also is intended to include other symptoms, such as cough and pain related to allergies, infections, colds, coughs, flu, viral and bacterial infections, and other common causes for the congestion. Thus, multiple symptoms including congestion may be treated with the compositions of the present invention. Treatment includes a reduction in severity or duration, delay in onset, and/or general relief of one or more of these symptoms. The term is intended to refer to congestion as described herein, as well as to a wide range of symptoms related to the congestion or its cause and treatable with the present compositions. For example, symptoms related to a common cold or flu such as cough, fever, and the like, and allergy symptoms such as hives, breakouts, swelling, and runny nose due to external stimulants are treated with the present compositions. In addition, symptoms, such as congestion, cough, pain and discomfort associated with the congestion, resulting from a bacterial or viral infection, particularly an infection in the respiratory tract, are also treated with the present compositions. The term "congestion", as use herein, is intended to refer to the narrowing of an airway including the oral, pharyngeal, nasal and bronchial passages due to fluid or a solid substance, such as mucus or phlegm. Narrowing of the airway is often due to swelling or inflammation of the mucous membrane lining the passage to result in a partially or fully blocked passage. Severe cases of congestion often cause difficulties in breathing. Besides allergic reactions, infections, and common cold and flu, the symptoms described herein may also be due to poor health or a predisposition for the symptom through genetic make-up. The terms "treating" and "alleviating", as used herein with respect to upper respiratory and oral pharyngeal congestion and related symptoms, include any reduction in severity or duration, of any degree, of the congestion and/or one or more of the related symptoms. The terms also include any delays in onset of and any general relief from the congestion and/or one or more of the related symptoms. Thus, the present invention encompasses palliative compositions and methods.

To this end, and in accordance with the principles of the present invention, the compositions include an antitussive, a decongestant, and an antihistamine consisting essentially of diphenhydramine or a pharmaceutically acceptable salt thereof, in a pharmaceutically acceptable dosage form. Inclusion of diphenhydramine as an antihistamine, in combination with an antitussive and a decongestant provides relief of histamine-stimulated allergy symptoms in addition to relieving other symptoms, such as cough, congestion, swelling, and pain. The inclusion of diphenhydramine allows the present composition to be useful in treating multiple allergy and cold-type symptoms in both children as well as adults with a single pharmaceutically acceptable dosage form while providing benefits beyond comparable antihistamines of the prior art. These added benefits provide increased efficacy and translate into convenience and cost savings for the patient. Further, a single ingredient providing so many benefits and physiological effects provides effective relief without the need to ingest multiple medications.

Diphenhydramine is the sole material and basic ingredient that provides antihistamine properties in the composition. Diphenhydramine is known primarily to provide antihistamine effects. However, in addition to its antihistamine properties, diphenyhydramine also provides secondary effects or other mild effects. Mild effects of an agent are of a secondary nature with respect to its primary effect or to the reason for administration. For example, diphenhydramine has been shown to be effective as a mild anticholinergic agent, acting in the central nervous system to slow down or depress nerve activity. To this end, diphenhydramine advantageously provides a sedative effect to cause drowsiness thereby helping the person get rest and plenty of needed sleep. Further, it has been shown that diphenhydramine is mildly effective as an analgesic for pain relief, and is a mild antitussive for suppression and relief of cough. Further, diphenhydramine has been shown to enhance the effects of an existing analgesic that may be included in the composition or independently administered to the person in need thereof. For example, as an analgesic adjuvant, diphenhydramine furthers the effect of opioids such as codeine, Tylenol®, ibuprofen, aspirin, or other commonly administered painkillers. Accordingly, diphenhydramine provides an analgesic effect, a sedative effect, an antitussive effect and an anticholinergic effect typically less than that of an active ingredient physiologically effective primarily as an analgesic, a sedative, an antitussive, or an anticholinergic agent. The antihistamines used in prior art medications fail to provide such as wide range of additional benefits. To this end, prior art medications must include additional ingredients or increased dosages of specific ingredients to provide the advantages of the present compositions.

Diphenhydramine is included in the composition in an effective amount to provide the relief described above to all persons, including children and adults. The term "effective amount" as used herein, is intended to refer to an amount effective for bringing about an improvement in the condition of, and/or relief from or treatment of one or more symptoms of upper respiratory and oral pharyngeal congestion. Further, the effective amount refers to an amount in a single dose of the formulation. The formulation may be ingested more than once per day for the relief desired, to sustain the relief desired, etc. An amount of the diphenhydramine proven to be effective is generally within the range from about 3 mg to about 100 mg in a single dose. Amounts greater than about 100 mg in a single dose may cause toxic side-effects in the patient, and amounts greater than about 300 mg in a single dose are very likely to cause toxicity. Clinically effective amounts are generally in the range from about 6 mg diphenhydramine to about 50 mg diphenhydramine in a single dose. For example, for children between the ages of 12–24 months, an effective amount is typically between about 3 mg to about 6 mg. For children between the ages of 2–6 years, an effective amount is typically about 6 mg. For children between the ages of 6–12 years, an effective amount is typically about 12 mg. It is not recommended to dose children below the age of 12 months with diphenhydramine. For adolescents and adults above the age of 12 years, an effective amount of diphenhydramine is typically in the range from about 12 mg to about 50 mg. In one embodiment, 25 mg of diphenhydramine is the amount in a single dose directed to the average adult patient.

To provide relief as an antihistamine, as well as relief as a mild analgesic, an analgesic adjuvant, a sedative, and a mild antitussive as described above, the amount of diphenhydramine in a single dose of the formulation may be in the mid to upper end of the ranges provided. Further, depending upon the particular formulation desired and/or the particular consumer targeted, the effective amount may vary. In one embodiment of the present invention, diphenhydramine is included in the composition in a range of about 3 mg to about 25 mg, useful for administration to a child. In another embodiment, the dosage of diphenhydramine is about 12 mg. In yet another embodiment, diphenhydramine is included in the composition in a range of about 12 mg to about 100 mg, useful for administration to an adult. In yet a further embodiment, the dosage of diphenhydramine is about 25 mg.

The present composition also includes an antitussive. The term "antitussive", as used herein, is intended to include any agent or active ingredient effective for cough suppression. These include, but are not limited to, common opioid analgesics such as hydrocodone, codeine, morphine, morphine-related compounds including diacetylmorphine, oxymorphone, hydromorphone, dextromethorphan, levorphanol, oxycodone, nalmefene, methadone, meperidine, pentazocine, buprenorphine, nalbuphine, butorphanol, sufentanyl, alfentanyl and propoxyphene, and opioid antagonists not structurally-related to morphine, such as nalorphine, naloxone, naltrexone and fentanyl. In one embodiment, the antitussive agent is hydrocodone or a pharmaceutically acceptable salt form thereof, such as hydrocodone bitartrate.

An effective amount of the antitussive in the composition is generally in the range from about 0.5 mg to about 15 mg in a single dose of the formulation. Clinically effective amounts are generally in the range from about 0.5 mg to about 10 mg. For example, for children between the ages of 2–6 years, an effective amount of codeine in a single dose is typically between about 0.5 mg to about 1 mg. For children between the ages of 6–12 years, an effective amount of hydrocodone in a single dose is typically between about 1 mg to about 2 mg. An antitussive agent is not recommended for administration to a child below the age of 2 years. For adolescents and adults above the age of 12 years, an effective amount of an antitussive in a single dose is typically in the range of about 2 mg to about 15 mg with about 5 mg being effective for an average adult patient. In one embodiment of the present invention, the antitussive is included in a single dose of the formulation in at least about 0.5 mg, and in another embodiment, in a range between about 0.5 mg to about 8 mg and targeted for treatment of cough and/or pain in a child. In another embodiment, the antitussive is included in a single dose of the formulation in a range of about 2 mg to about 15 mg, and in yet another embodiment, in a weight of about 5 mg, and targeted for treatment of cough and/or pain in an adult.

The present composition also includes a decongestant. The term "decongestant" as used herein, is intended to refer to any agent or ingredient, active for reducing or eliminating congestion of the air passages by widening the airway, and/or by stimulating the release of phlegm and mucus from these passages. Air passages may be widened by reducing the swelling of the mucous membranes in the passage. Generally, sympathomimetic drugs have decongestant properties. Examples of suitable decongestants include, without limitation, phenylethylamine, epinephrine, norepinephrine, dopamine, dobutamine, colterol, ethylnorepinephrine, isoproterenol, isoetharine, metaproterenol, terbutaline, metaraminol, phenylephrine, tyraine, hydroxyamphetamine, ritodrine, prenalterol, methoxyamine, albuterol, amphetamine, methamphetamine, benzphetamine, ephedrine, phenylpropanolamine, mephentermine, phentermine, fenfluramine, propylhexedrine, diethylpropion, phenmetrazine, phendimetrazine, oxymetazoline, xylometazoline, and pseudoephedrine. An effective amount of the decongestant is generally within the range of about 1 mg to about 20 mg in a single dose of the formulation. Where the composition is directed towards relief of congestion and related symptoms in a child, an effective amount of the decongestant is typically in a dosage range of about 1 mg to about 10 mg. In one embodiment, the amount in a single dose is about 4 mg. For example, for a child between the ages of 2–6 years, an effective amount of phenylephrine is an amount in the range of about 1 mg to about 4 mg in a single dose. For a child between the ages of 6–12 years, an effective amount of phenylephrine is an amount in the range of about 4 mg to about 10 mg in a single dose. It is not recommended to dose a child under the age of 2 with phenylephrine. Where the composition is targeted for treating congestion and related symptoms in an adolescent above 12 years of age and in an adult, an effective amount of the decongestant in a single dose is typically in a range from about 5 mg to about 20 mg. In various embodiments, the amount in a single dose is about 7 mg for a teenager, and about 10 mg for an adult. In one embodiment, the decongestant is phenylephrine and included in a single dose of the formulation in an amount of at least 1 mg, and in another embodiment, is included in a single dose in an amount in the range of about 1 mg to about 20 mg. In yet another embodiment, the decongestant is phenylephrine and is included in a single dose in an amount of about 4 mg in a formulation designed to treat upper respiratory and oral pharyngeal congestion in a child. In yet a further embodiment, the decongestant is phenylephrine and is included in a single dose in an amount of about 10 mg in a formulation designed to treat upper respiratory and oral pharyngeal congestion in an adult.

It should be understood that an effective amount of the antitussive and the decongestant generally vary with the particular antitussive and decongestant chosen. In addition, an effective amount depends upon many other factors, such as known differences in pharmacokinetic parameters (absorption, distribution and clearance) regardless of the cause. For example, in a patient with a renal disfunction or disorder, the effective dose of the diphenhydramine, the antitussive, and the decongestant is generally half of an effective dose for a patient without renal disfunction. Further, it is recommended that the dose of the diphenhydramine, the antitussive, and the decongestant be ingested 4–6 times daily for effective relief of symptoms over a 24 hour period. Accordingly, toxic side effects from excess amounts of one or more of the active ingredients may be experienced by patients ingesting more than the recommended daily amounts of the composition within a 24 hour period, or in patients with the previously described disorders.

While the present composition includes an antitussive, a decongestant, and diphenhydramine as an antihistamine, the present composition is not so limited and may include other components. These components include conventional excipients, useful and/or desirable to render the composition suitable or attractive for consumption and use. Excipients providing physical and aesthetic properties for formulation or delivery of the composition are desirable. For example, with respect to physical properties, ingredients imparting desirable and acceptable hardness, disintegration properties, dissolution rate for release of therapeutic components, stability, and size to effectively deliver the composition may be included. Disintegrants may be included for the purposes of facilitating the breakup of a tablet after the tablet is administered to the patient. Examples of disintegrants include, but are not limited to, modified or unmodified starches such as cornstarch, potato starch, wheat starch, or sodium crosscarmellos. With respect to aesthetics, it may be desirable for the composition to contain additives that appeal to the human senses such as colorants, fragrances, texture modifiers, and/or flavorants. Additionally, many flavoring agents such as, for example, fruit flavors, or sweeteners, such as sodium saccharin, confectionery sugar, sucrose, xylitol, or combinations thereof, may be included. Additionally, suitable colorants including, for example, red beet powder, ferric oxide, FD&C dyes, or combinations thereof, may be included in the present compositions. Desirable excipients may also include buffering agents, surfactants, electrolytes, and thixotropic agents. It should be understood that these other components should not affect the action or mechanism of action of the antitussive, decongestant, and/or the diphenhydramine in the composition.

Excipients or formulations affecting the release properties, mechanisms, and/or rates of the antitussive, the decongestant, and the diphenhydramine, from the composition upon oral ingestion may be provided. For example, the composition may be formulated such that the release of the antitussive, the decongestant, and/or the diphenhydramine or other active ingredients from the composition is delayed for a period of time or to survive a particular environment. Advantageously, the composition may be formulated so as to prevent the release of the antitussive, the decongestant, and/or the diphenhydramine in the stomach where they may likely be acidified, salted out and excreted from the body rather than absorbed into the circulation. For example, the composition may be coated with a coating to improve absorption and render the composition more bioavailable than it would otherwise be without the coating. Enteric coatings or encapsulation-type coatings as known to one skilled in the art are suitable for this purpose. In one embodiment, a table or a capsule form of the composition is enterically coated so as to provide delayed-release and sustained-release properties to the composition. Sustaining the release of individual active ingredients to the body over a period of time prolongs the effective time period of relief from the congestion and related symptoms, provided, however, the amount of the ingredient in the blood stream is within the effective therapeutic window for that particular ingredient. Further, preservatives may be provided to prevent degradation of components in the composition or degradation of the composition as a whole, thereby improving the stability and prolonging the shelf life of the composition.

The composition of the present invention may be formulated in a single form. In one embodiment, the form is convenient to swallow, and has a generally accepted appearance and taste to promote consumption and compliance with a dosing regimen. In accordance with one aspect of the present invention, the composition is formulated into a dosage form that may be an ingestible liquid, a pill, a tablet, a capsule, a suppository, etc. In accordance with another aspect of the invention, the composition may be formulated into a parenterally administrable form. It should be understood by one skilled in the art that certain active agents, such as hydrocodone, are typically not parenterally administered, such as by intra-venous administration. However, other opioids such as codeine, morphine, methadone, and fentanyl may be administered with diphenhydramine in a non-orally administrated formulation. In accordance with a further aspect of the invention, the present composition may include active ingredients suitable for sub-lingual administration. In accordance with yet another aspect of the invention, the present composition may be administered via mucous membranes of the buccal, nasal, rectal cavities, etc. The desired formulation may be prepared by a process known in the art of pharmaceutical manufacture. For example, liquid formulations may be prepared in the form of a syrup or a suspension. In one embodiment, the composition is formulated into an elixir or a syrup having a desirable flavor for easy, trouble-free administration to a child.

Solid formulations, such as capsules may be prepared by first blending the antitussive, the decongestant, and the diphenhydramine with other desirable additives and then filling capsular materials with the blended mixture using conventional filling equipment. In one embodiment, the capsular material is a gelatin. The capsule formed may be a liquid gelatin capsule. Further, where desired, the capsule may be coated for added benefits. In general, tablets may be formed by first blending the components and then either directly compressing the blended components, or granulating the components followed by compressing them into a tablet form. Additional ingredients may be included during compression where desired. For example, the granular mixture may contain one or more lubricants to inhibit sticking during compression. Examples of suitable lubricants include, but are not limited to, stearic acid, palmetic acid, stearates, talc, and oils.

To effectively suppress cough, relieve pain, and reduce mucus membrane swelling for reducing congestion and other blockage of air passages, the composition of the present invention includes the antitussive, the decongestant, and the diphenhydramine in amounts suitable for treating children and adults alike. To this end, in one embodiment of the invention, a single dose of the formulation includes hydrocodone or a pharmaceutically acceptable salt, such as a bitartrate salt, as an antitussive in a range from about 0.5 mg to about 15 mg, phenylephrine or a pharmaceutically acceptable salt thereof as a decongestant in a range from about 1 mg to about 20 mg, and diphenhydramine or a pharmaceutically acceptable salt thereof in a range from about 3 mg to about 100 mg. In another embodiment, a single dose of the formulation includes hydrocodone or a pharmaceutically acceptable salt thereof in a weight of about 2 mg, phenylephrine or a pharmaceutically acceptable salt in a weight of about 7 mg, and diphenhydramine or a pharmaceutically acceptable salt in a weight of about 12 mg, for treatment of upper respiratory and oral pharyngeal congestion and related symptoms in a child aged 6 to 12 years (a single dose or one teaspoon where the formulation is a liquid) or in an adult (twice the children's dose or two teaspoons if formulated as a liquid). In yet another embodiment, a single dose includes hydrocodone or a pharmaceutically acceptable salt in a weight of about 5 mg, phenylephrine or a pharmaceutically acceptable salt in a weight of about 10 mg, and diphenhydramine or a pharmaceutically acceptable salt in a weight of about 25 mg in a dosage formulation suitable for treatment of upper respiratory and oral pharyngeal congestion and related symptoms in an adult.

In yet another embodiment of the present invention, there is provided methods of alleviating symptoms of upper respiratory and oral pharyngeal congestion by orally administering to a patient in need thereof a single dose of a composition or formulation including an antitussive, a decongestant, and diphenhydramine or a pharmaceutically salt thereof as an antihistamine. The patient in need may be a child or an adult suffering from the congestion. Administration of the composition will depend upon the form of the composition. For example, a liquid formulation may be administered to a child in amounts smaller than that administered to an adult. Administration will also depend upon various other factors related to the patient. For example, age, health, weight, prior medical history, extent and degree of symptoms, and overall medical diagnosis will generally influence the amounts administered. The composition is generally administered for alleviating cough, pain, cold and allergy symptoms and also provides a sedative effect, an analgesic adjuvant effect, an anti-cholinergic affect, and a mild analgesic effect.

While the present invention has been illustrated by the description of embodiments thereof, and while the embodiments have been described in considerable detail, it is not intended to restrict or in any way limit the scope of the appended claims to such detail. Additional advantages and modifications will be readily apparent to those skilled in the art. The invention in its broader aspects is, therefore, not limited to the specific details, representative method, and illustrated examples described. Accordingly, departures may be made from such details without departing from the scope or spirit of Applicant's general inventive concept.

What is claimed is:

1. A pediatric pharmaceutical composition for alleviating symptoms of upper respiratory and oral-pharyngeal congestion in a pediatric patient comprising an antitussive analgesic opioid or opiate, a decongestant, and an antihistamine having analgesic adjuvant effects selected from the group consisting of diphenhydramine, a pharmaceutically acceptable salt thereof, and a mixture thereof, the composition in a pharmaceutically acceptable formulation.

2. The composition of claim 1 wherein the antitussive analgesic opioid or opiate is present in a single dose of the formulation in a weight of at least about 0.5 mg.

3. The composition of claim 1 wherein the antitussive analgesic opioid or opiate is present in a single dose of the formulation in a weight range from about 0.5 mg to about 15 mg.

4. The composition of claim 1 wherein the decongestant is present in a single dose of the formulation in a weight of at least about 1 mg.

5. The composition of claim 1 wherein the decongestant is present in a single dose of the formulation in a weight range from about 1 mg to about 20 mg.

6. The composition of claim 1 wherein the antitussive analgesic opioid or opiate is hydrocodone or a pharmaceutically acceptable salt thereof.

7. The composition of claim 6 wherein hydrocodone is present in a single dose of the formulation in a weight range from about 0.5 mg to about 15 mg.

8. The composition of claim 1 wherein the decongestant is phenylephrine or a pharmaceutically acceptable salt thereof.

9. The composition of claim 8 wherein phenylephrine is present in a single dose of the formulation in a weight range from about 1 mg to about 20 mg.

10. The composition of claim 1 wherein diphenhydramine is present in a single dose of the formulation in a weight of at least about 3 mg.

11. The composition of claim 1 wherein diphenhydramine is present in a single dose of the formulation in a weight range from about 3 mg to about 100 mg.

12. The composition of claim 1 wherein:
  the antitussive analgesic opioid or opiate is hydrocodone or a pharmaceutically acceptable salt thereof present in a single dose of the formulation in a weight range from about 0.5 mg to about 15 mg;
  the decongestant is phenylephrine or a pharmaceutically acceptable salt thereof present in a single dose of the formulation in a weight range from about 1 mg to about 20 mg; and
  the diphenhydramine or pharmaceutically acceptable salt thereof is present in a single dose of the formulation in a weight range from about 3 mg to about 100 mg.

13. The composition of claim 1 wherein:
  the antitussive analgesic opioid or opiate is hydrocodone or a pharmaceutically acceptable salt thereof present in a single dose of the formulation in a weight range from about 0.5 mg to about 8 mg;

the decongestant is phenylephrine or a pharmaceutically acceptable salt thereof present in a single dose of the formulation in a weight range from about 1 mg to about 10 mg; and the diphenhydramine or pharmaceutically acceptable salt thereof is present in a single dose of the formulation in a weight range from about 3 mg to about 25 mg.

14. The composition of claim 1 wherein:

the antitussive analgesic opioid or opiate is hydrocodone or a pharmaceutically acceptable salt thereof present in a single dose of the formulation in a weight range from about 2 mg to about 15 mg;

the decongestant is phenylephrine or a pharmaceutically acceptable salt thereof present in a single dose of the formulation in a weight range from about 5 mg to about 20 mg; and the diphenhydramine or pharmaceutically acceptable salt thereof is present in a single dose of the formulation in a weight range from about 12 mg to about 100 mg.

15. The composition of claim 1 wherein the formulation is selected from the group consisting of a liquid, a pill, a tablet, a capsule and a suppository.

16. The composition of claim 15 wherein the tablet is selected from the group consisting of a chewable tablet, a melting tablet, and an enteric-coated tablet.

17. The composition of claim 15 wherein the capsule is selected from the group consisting of a liquid gelatin capsule and an enteric-coated capsule.

18. The composition of claim 1 wherein the formulation is a liquid.

19. The composition of claim 1 wherein the formulation is adapted to prevent release of the antitussive analgesic opioid or opiate, the decongestant, and the diphenhydramine or pharmaceutically acceptable salt thereof in the stomach.

20. The composition of claim 1 in a slow-release formulation adapted to release the antitussive analgesic opioid or opiate, the decongestant, and the diphenhydramine or pharmaceutically acceptable salt thereof over a period of time.

21. The composition of claim 1 wherein the diphenhydramine or pharmaceutically acceptable salt thereof is present in an amount sufficient to provide combined antihistamine and anti-cholinergic effects in a patient.

22. The composition of claim 1 wherein the diphenhydramine or pharmaceutically acceptable salt thereof is present in an amount sufficient to provide combined antihistamine and antitussive effects in a patient.

23. The composition of claim 1 wherein the diphenhydramine or pharmaceutically acceptable salt thereof is present in an amount sufficient to provide combined antihistamine and analgesic effects in the patient.

24. The composition of claim 1 wherein the diphenhydramine or a pharmaceutically acceptable salt thereof is present in an amount sufficient to provide combined antihistamine and sedative effects in the patient.

25. A pediatric pharmaceutical composition for alleviating symptoms of upper respiratory and oral-pharyngeal congestion in a pediatric patient consisting essentially of:

an antitussive analgesic opioid or opiate present in a weight of at least about 0.5 mg;

a decongestant present in a weight of at least about 1 mg; and diphenhydramine or a pharmaceutically acceptable salt thereof having analgesic adjuvant effects present in a weight of at least about 3 mg, in a pharmaceutically acceptable single dose formulation.

26. The composition of claim 25 wherein:

the antitussive analgesic opioid or opiate is hydrocodone or a pharmaceutically acceptable salt thereof present in a weight up to about 15 mg;

the decongestant is phenylephrine or a pharmaceutically acceptable salt thereof present in a weight up to about 20 mg; and diphenhydramine or a pharmaceutically acceptable salt thereof is present in a weight up to about 100 mg.

27. The composition of claim 25 wherein:

the antitussive analgesic opioid or opiate is hydrocodone or a pharmaceutically acceptable salt thereof present in a weight up to about 8 mg;

the decongestant is phenylephrine or a pharmaceutically acceptable salt thereof present in a weight up to about 10 mg; and the diphenhydramine or pharmaceutically acceptable salt thereof is present in a weight up to about 25 mg.

28. The composition of claim 25 wherein:

the antitussive analgesic opioid or opiate is hydrocodone or a pharmaceutically acceptable salt thereof present in the formulation in a weight range from about 2 mg to about 15 mg;

the decongestant is phenylephrine or a pharmaceutically acceptable salt thereof present in the formulation in a weight range from about 5 mg to about 20 mg; and the diphenhydramine or pharmaceutically acceptable salt thereof is present in the formulation in a weight range from about 12 mg to about 100 mg.

29. The composition of claim 25 wherein the formulation is selected from the group consisting of a liquid, a pill, a tablet, a capsule and a suppository.

30. The composition of claim 25 wherein the formulation is a liquid.

31. A pediatric composition for alleviating symptoms of upper respiratory and oral-pharyngeal congestion in a pediatric patient consisting essentially of hydrocodone, phenylephrine, and diphenhydramine or a pharmaceutically acceptable salt thereof having analgesic adjuvant effects in a pharmaceutical formulation.

32. The composition of claim 31 wherein:

the hydrocodone or a pharmaceutically acceptable salt thereof is present in a single dose of the formulation in a weight of about 2 mg;

the phenylephrine or a pharmaceutically acceptable salt thereof is present in a single dose of the formulation in a weight of about 7 mg; and the diphenhydramine or a pharmaceutically acceptable salt thereof is present in a single dose of the formulation in a weight of about 12 mg.

33. The composition of claim 31 wherein:

the hydrocodone or a pharmaceutically acceptable salt thereof is present in a single dose of the formulation in a weight of about 5 mg;

the phenylephrine or a pharmaceutically acceptable salt thereof is present in a single dose of the formulation in a weight of about 10 mg; and the diphenhydramine or a pharmaceutically acceptable salt thereof is present in a single dose of the formulation in a weight of about 25 mg.

34. A pediatric palliative method for alleviating symptoms of upper respiratory and oral-pharyngeal congestion in a patient comprising orally administering to a pediatric patient in need thereof a single dose formulation of a composition comprising an effective amount of an antitussive analgesic opioid or opiate, an effective amount of a decongestant, and an effective amount of an antihistamine having analgesic adjuvant effects selected from the group consisting of diphenhydramine, a pharmaceutically acceptable salt thereof, and a mixture thereof, at dosing intervals.

35. The method of claim 34 wherein said symptoms to be alleviated are symptoms of at least one of an allergy, a cold, a pain, a cough, and an upper-respiratory infection.

36. The method of claim 34 wherein diphenhydramine is present in an amount sufficient to provide at least one of a mild antitussive effect, a mild analgesic effect, a sedative effect, an anti-cholinergic effect, and an analgesic adjuvant effect in the patient.

37. The method of claim 34 wherein the antitussive analgesic opioid or opiate is hydrocodone or a pharmaceutically acceptable salt thereof and is present in a weight of at least about 0.5 mg.

38. The method of claim 34 wherein the antitussive analgesic opioid or opiate is hydrocodone or a pharmaceutically acceptable salt thereof and is present in a weight range from about 0.5 mg to about 15 mg.

39. The method of claim 34 wherein the decongestant is phenylephrine or a pharmaceutically acceptable salt thereof and is present in a weight of at least about 1 mg.

40. The method of claim 34 wherein the decongestant is phenylephrine or a pharmaceutically acceptable salt thereof and is present in a weight range from about 1 mg to about 20 mg.

41. The method of claim 34 wherein the diphenhydramine or a pharmaceutically acceptable salt thereof is present in a weight of at least about 3 mg.

42. The method of claim 34 wherein the diphenhydramine or a pharmaceutically acceptable salt thereof is present in a weight range from about 3 mg to about 100 mg.

43. The method of claim 34 wherein the single dose formulation is selected from the group consisting of a liquid, a pill, a tablet, a capsule and a suppository.

44. The method of claim 43 wherein the single dose formulation is coated to prevent release of the antitussive analgesic opioid or opiate, the decongestant, and the diphenhydramine or pharmaceutically acceptable salt thereof from the composition in the stomach.

45. The method of claim 34 wherein the composition administered is a chewable tablet, a melt tablet, an enteric-coated tablet, a liquid gelatin capsule, and an enteric-coated capsule.

46. The method of claim 34 wherein:
the antitussive analgesic opioid or opiate is hydrocodone or a pharmaceutically acceptable salt thereof and is present in the composition administered in a weight range from about 0.5 mg to about 15 mg;
the decongestant is phenylephrine or a pharmaceutically acceptable salt thereof and is present in the composition administered in a weight range from about 1 mg to about 20 mg; and
the diphenhydramine or a pharmaceutically acceptable salt thereof is present in the composition administered in a weight range from about 3 mg to about 100 mg.

47. The method of claim 46 wherein the composition is directed for administration to a child.

48. A pediatric palliative method for alleviating symptoms of upper respiratory and oral-pharyngeal congestion in a patient comprising orally administering to a pediatric patient in need thereof a composition comprising an effective amount of an antitussive analgesic opioid or opiate, an effective amount of a decongestant, and an effective amount of an antihistamine having analgesic adjuvant effects selected from the group consisting of diphenhydramine, a pharmaceutically acceptable salt thereof, and mixtures thereof, and not containing an expectorant.

49. A pediatric palliative method for alleviating symptoms of upper respiratory and oral-pharyngeal congestion in a patient comprising orally administering to a pediatric patient in need thereof a composition comprising an effective amount of an antitussive analgesic opioid or opiate, an effective amount of a decongestant, and an effective amount of diphenhydramine providing combined antihistamine, analgesic adjuvant, and anticholinergic effects in the patient.

50. The method of claim 49 wherein the diphenhydramine further provides an antitussive effect.

51. The method of claim 49 wherein the diphenhydramine further provides an analgesic effect.

52. The method of claim 49 wherein the diphenhydramine further provides a sedation effect.

53. A pediatric palliative method for alleviating symptoms of upper respiratory and oral-pharyngeal congestion in a pediatric patient comprising orally administering to a pediatric patient in need thereof a composition comprising an effective amount of an antitussive analgesic opioid or opiate, an effective amount of a decongestant, and an effective amount of a single compound providing combined antihistamine, anticholinergic, and analgesic adjuvant effects in the patient.

* * * * *